United States Patent [19]

Sales et al.

[11] Patent Number: 5,782,955
[45] Date of Patent: Jul. 21, 1998

[54] LOW OXYGEN-CONTENT METALLURGICAL SILICON AND FERROSILICON

[75] Inventors: Maurice Sales, Annecy; Thomas Margaria, Passy, both of France

[73] Assignee: Pechiney Electrometallurgie, Courbevoie, France

[21] Appl. No.: 584,430

[22] Filed: Jan. 11, 1996

[30] Foreign Application Priority Data

Jan. 9, 1995 [FR] France ................... 95 00330

[51] Int. Cl.$^6$ ................... C22C 29/18
[52] U.S. Cl. ................... 75/255; 75/252; 420/578
[58] Field of Search ................... 75/252, 255; 420/578; 423/324, 348

[56] References Cited

U.S. PATENT DOCUMENTS

| | | | |
|---|---|---|---|
| 4,532,090 | 7/1985 | Dietze et al. | 264/14 |
| 5,094,832 | 3/1992 | Forwald et al. | 423/348 |
| 5,532,063 | 7/1996 | Shindoh et al. | 75/252 |
| 5,605,583 | 2/1997 | Margaria et al. | 423/348 |

FOREIGN PATENT DOCUMENTS

| | | | |
|---|---|---|---|
| 1222125 | 5/1987 | Canada | 423/348 |
| 1169508 | 12/1958 | France . | |
| 3405613 A1 | 8/1985 | Germany . | |

OTHER PUBLICATIONS

ASM Handbook, vol. 2, Properties and Selection, pp. 1154–1155, ASM, 1990.

Filipovich et al., "Proceedings of International Symposium on Ferro–Alloys and Silicon Metal", Sep. 17–21, 1975.

Primary Examiner—George Wyszomierski

[57] ABSTRACT

A metallurgical silicon or ferrosilicon in the form of granulates having an average size of less than 10 mm and in which the total oxygen concentration is less than 0.05% by weight, and a process for manufacture of this silicon or ferrosilicon consisting of a carbothermal reduction of silica in an electric oven, chlorine-based refining of the liquid metal, and granulation of the refined liquid metal in water under an inert atmosphere. The silicon may be used for silicone manufacture or as a constituent of an aluminum alloy, and the ferrosilicon, as a steel additive used to obtain magnetic sheet metals for electrical construction.

10 Claims, No Drawings

LOW OXYGEN-CONTENT METALLURGICAL SILICON AND FERROSILICON

FIELD OF THE INVENTION

The invention relates to metallurgical silicon i.e., silicon obtained by carbothermal reduction of silica in an electric oven and intended mainly for the manufacture of silicones, of aluminum-silicon alloys, and of high-purity ferrosilicon obtained by carbothermal reduction of silica in the presence of scrap iron and intended, in particular, for the manufacture of magnetic sheet steel used for transformers.

BACKGROUND OF THE INVENTION

The synthesis of alkyl or aryl halogenosilanes by reacting a halogenated hydrocarbon on silicon in the presence of copper at between 250° and 350° C. has been known since U.S. Pat. No. 2,380,995 was issued to E. G. Rochow on Aug. 7, 1945.

This reaction, called the Rochow reaction, has achieved wide-spread industrial use, and constitutes, in particular, the basic reaction used in the silicone industry. This reaction is normally conducted using methyl chloride $CH_3Cl$, and yields a mixture of various methylchlorosilanes in varying proportions. The oxygen content of the silicon used in this synthesis affects the outcome in several ways:

the oxygen fixed at the surface of the silicon forms a barrier which slows the reaction, and, therefore, the productivity of the particular reaction vessel. Accordingly, in European Patent No. EP 0494837 the applicant disclosed a metallurgical silicon powder exhibiting low surface oxidation and having a surface protected from oxidation by an organic substance.

the oxygen contained within the mass is most notably present in the form of slag inclusions, the slag being formed mainly from oxides. This slag, while not affecting directly the kinetics of the Rochow reaction, has the disadvantage of leaving an inert residue which may accumulate in industrial-scale reaction vessels and reduce the usable volume thereof, an occurrence which remains undetected when efforts are confined to assessing silicon quality by means of laboratory tests.

In addition, in metallurgy, the manufacture of aluminum-silicon alloys also requires base materials having low oxygen contents, since slag inclusions in the finished alloy adversely affect mechanical properties.

Finally, as regards the manufacture of magnetic sheet metals intended for transformers and electrical rotating machines, use is made of a ferrosilicon containing very low proportions of impurities and a low oxygen content, which favorably affects magnetic permeability.

For these different reasons, it appeared necessary to propose a silicon or ferrosilicon having a low oxygen content, both on the surface and within the mass.

Silicon and ferrosilicon manufactured by carbothermal reduction of silica in an electric oven contain various impurities, in particular calcium and aluminum, which are subsequently removed by oxidizing refining. This refining process can be performed using chlorine or oxygen.

M. Filipovich and F. Mulalich presented the comparative results of these two types of refining procedure to the International Symposium on the Production of Ferroalloys and of Silicon, held in Sibenik, Yugoslavia, on Sep. 17–21, 1975.

Because the use of chlorine poses safety and environmental problems, silicon and ferrosilicon are normally refined using oxygen. The product thus contains more than 0.25% oxygen despite the precautions taken to separate the metal from the slag.

The refined liquid silicon or ferrosilicon may be poured and solidified in different ways. For example, the search for specific structures used in silicone-related applications has prompted control of solidification and cooling rates.

One technique which has been recently applied to silicon consists in granulating the product in water, i.e., in pouring molten silicon at about 1,500° C. directly into water. This procedure produces well-structured crystallization, but also totally undesirable, pronounced surface oxidation of the silicon crystals.

To avoid this problem, the applicant has, in its French Patent Application No. 93-10257, proposed conducting this granulation operation in an inert atmosphere. In this way, it is possible to obtain silicon containing less than 0.15% oxygen and in which the surface oxygen concentration is 100 ppm. However, this total oxygen content is still excessively high.

SUMMARY OF THE INVENTION

The invention relates to a metallurgical silicon or ferrosilicon of high purity, in the form of granulates measuring less than 10 mm, or of a powder having a granulometry of less than 0.4 mm, and in which the total oxygen content is less than 0.05% (by weight). To achieve a concentration this low, the inventors conceived of combining (a) chlorine-based refining of the liquid silicon or ferrosilicon with (b) granulation in water under an inert atmosphere. Neither of these processes alone is capable of achieving a similar level of purity.

DESCRIPTION OF PREFERRED EMBODIMENT

In the granular state, the silicon or ferrosilicon according to the invention has a total oxygen concentration of less than 0.05%, which breaks down into a concentration of approximately 0.01% oxygen at the surface of the granulates and less than 0.04% within the mass.

The powdered product produced by grinding the granulates exhibits surface oxidation which is not uniformly distributed, the surface after grinding being, on average, less oxidized than that of the granulates.

The high-purity ferrosilicon has an Si content of between 60 and 80% (by weight), the most widely used compositions having a proportion of between 65 and 75%.

The silicon used for silicone manufacture may be combined with other elements, such as copper present up to a percentage of 8%, or phosphorous up to 0.2%, these elements being catalyst promoters of the Rochow reaction. This silicon contains less than 0.5% iron, less than 0.3% aluminum, and less than 0.10% calcium, the concentrations of Al and Ca being adjustable to predetermined values so as to obtain within the microstructure intermetallic compounds which promote the Rochow reaction.

The low overall oxygen content of the products according to the invention is achieved by combining chlorine-based refining of the liquid metal and the granulation thereof in water under an inert atmosphere.

If chlorine-based refining is effected on a silicon prepared in an induction oven in a vacuum by incorporating Ca and Al in the metallic state into electronic-quality silicon, residual concentrations of less than 0.05% Ca and less than 0.12% Al are obtained.

If, on the contrary, the starting silicon contains slag inclusions in suspension, a phenomenon which always occurs in liquid silicon prepared by carbothermia in an electric oven, the residual concentrations of Ca and Al existing after chlorine treatment result mainly from the presence of slag inclusions on which the chlorine treatment has no effect, since $Al_2O_3$ and CaO oxides are involved.

The results reported by Filipovich and Mulalich in the paper mentioned above point to an average residual Ca concentration of 0.39% with a standard deviation of 0.24%, a value which can be explained only by a variable average oxygen concentration of 0.17%.

Chlorine-based refining may utilize gaseous chlorine, but also a chlorinated compound, such as $CCl_4$ or $C_2Cl_6$.

Granulation in water can take place by pouring the liquid ferrosilicon or silicon into a chute comprising a hole, the metal stream emanating from this orifice breaking up on a horizontal cupel positioned beneath the hole and being divided into liquid drops which then fall into a container filled with cooling water. The drops thus formed are solidified and collected on the bottom of the container. The upper part of the container, in which the cupel is placed, is swept by a current of inert gas, which may be nitrogen or an air/nitrogen mixture.

It is found that combining this type of granulation and chlorine-based refining of the molten metal produces an oxygen content which is appreciably lower than that of metallurgical silicon or ferrosilicon prepared according to all processes of the prior art.

The granulates thus obtained, whose average size is less than 10 mm, may be ground in the form of a powder having an average granulometry of less than 0.4 mm, by making preferred use of a grinding additive protecting the product from oxidation. As regards silicon, Applicant's EP 0494837 recommends grinding under a minimally-reactive atmosphere, for example of argon, nitrogen, or an air/nitrogen mixture, in the presence of an oil, which may be an alkane, an ester, a fatty substance, or a silicone oil. If silicon is used to manufacture silicones, this oil must be soluble in methyl chloride or be volatile at 300° C. The quantity of additive remaining in the ground product is generally less than 1% by weight.

EXAMPLE 1

A pouring ladle filled with molten silicon obtained by silica carboreduction in an electric oven was carefully decanted into a heated ladle in order to separate the molten silicon from the slag taken from the oven. The ladle containing molten silicon thus obtained was treated by oxygen injection, in order to oxidize the calcium and aluminum. The slag formed during refining was separated from decantation when the molten silicon was poured into ingot molds.

The product was then cooled, crushed, then ground to a granulometry of less than 0.4 mm in rod mills under a nitrogen atmosphere and with the addition of 0.3% glycerol tristearate.

During a manufacturing run, during which the operations were linked in sequence while taking care to clean the ladle after each pouring procedure, an analysis of the oxygen content of the silicon, measured for each pouring operation, was carried out for an entire day. To measure the total oxygen content, the specimen was ground to a granulometry of 0.25 mm, then sifted at 0.05 mm so as to retain only the 0.25–0.05 mm fraction. In fact, at the time of the preparation procedure, the fraction measuring less than 0.05 mm underwent additional oxidation, which could not be taken into consideration.

A 250-mg test sample was collected from the 0.25–0.05 mm fraction, then packaged in a tin sheet in order to be placed in the graphite crucible of a LECO device at a temperature of 3,000° C. The oxygen in the sample was transformed into CO, which was then oxidized so as to form $CO_2$, which was then analyzed. The final result was calculated based on the average obtained from five operations.

To obtain the surface oxygen content, the same treatments were carried out on electronic-quality silicon. Since the oxygen content within the mass of the product was virtually nil, the total concentration as measured corresponded to the surface content, which was the same as that of a sample of metallurgical silicon subjected to the same treatment.

The 12 pouring operations effected during the day yielded the following total oxygen concentrations:

| 0.24% | 0.21% | 0.25% | 0.20% |
|-------|-------|-------|-------|
| 0.23% | 0.26% | 0.24% | 0.23% |
| 0.25% | 0.22% | 0.24% | 0.23% |
| Average: 0.23% | | | |

EXAMPLE 2

During a granulation-testing run, the total oxygen content in the silicon was monitored during a one-day manufacturing period.

The preparation process consisted of the same steps as in the preceding example; however, instead of pouring the product into ingot molds, it was granulated in water under a nitrogen atmosphere.

The twelve pouring operations effected during the day yielded the following total oxygen contents:

| 0.14% | 0.11% | 0.09% | 0.11% |
|-------|-------|-------|-------|
| 0.12% | 0.13% | 0.14% | 0.10% |
| 0.11% | 0.09% | 0.12% | 0.11% |
| Average: 0.114% | | | |

EXAMPLE 3

Approximately 13 kg refined metal silicon, to which 70 g calcium and 130 g aluminum were added after melting, were melted in a laboratory induction oven. The molten bath was then treated with chlorine added at a flow rate of 30 /l mn. The treatment lasted five minutes.

The analyses of Ca, Al, and $O_2$ were performed on a sample collected directly from the molten metal by suctioning into a graphite tube, in which the metal solidified. Four tests of this type gave the following results:

| Test | Al % | Ca ppm | $O_2$ ppm |
|------|-------|--------|-----------|
| 1 | 0.086 | 40 | 88 |
| 2 | 0.140 | 52 | 90 |
| 3 | 0.100 | 49 | 99 |
| 4 | 0.140 | 47 | 121 |
| Average | 0.127 | 47 | 100 |

EXAMPLE 4

The conditions in Example 1 were repeated, and oxygen-based refining was replaced by chlorine refining.

The total oxygen analyses gave the following results:

| 0.17% | 0.15% | 0.12% | 0.16% |
|---|---|---|---|
| 0.11% | 0.14% | 0.13% | 0.18% |
| 0.12% | 0.15% | 0.11% | 0.14% |
| | Average: 0.14% | | |

In comparison with Example 3, it can be seen that working with molten silicon as obtained by carbothermia and poured in air caused the loss of a significant part of the gain as regards final oxygen content that should have been achieved using chlorine-based refining.

EXAMPLE 5

The operating conditions in Example 2 were repeated, but oxygen refining was replaced by chlorine refining, and the oxygen contents obtained during a one-day manufacturing period were once again analyzed, giving the following results:

| 530 ppm | 517 ppm | 498 mm | 507 ppm |
|---|---|---|---|
| 485 ppm | 525 ppm | 512 ppm | 470 ppm |
| 490 ppm | 505 ppm | 520 ppm | 485 ppm |
| | Average total oxygen: 504 ppm | | | of which approximately 100 ppm were identified as being caused by surface oxidation.

What is claimed is:

1. Metallurgical silicon or ferrosilicon in the form of granules having an average size of less than 10 mm, with a total oxygen content of less than 0.05% by weight, said total oxygen content including about 0.01% by weight derived from oxygen present in a surface layer of said granules, and less than about 0.04% by weight oxygen present in an inner mass of said granules.

2. Silicon according to claim 1, wherein the iron content thereof is less than 0.5%.

3. Silicon according to claim 1, wherein the aluminum content thereof is less than 0.3%.

4. Silicon according to claim 1, wherein the calcium content thereof is less than 0.10%.

5. Silicon according to claim 1, wherein said silicon contains a copper content of up to 8%.

6. Silicon or ferrosilicon according to claim 1, wherein said silicon or ferrosilicon has been ground into a powder having a granulometry of less than 0.4 mm and contains a grinding additive in a proportion of less than 1%.

7. Silicon according to claim 6, wherein the additive is an organic product soluble in methyl chloride and/or volatile at 300° C.

8. Silicon according to claim 1, which is useful as the raw material for the synthesis of alkyl or aryl halogenosilanes.

9. Silicon according to claim 1, which is useful as a constituent of an aluminum/silicon alloy.

10. Ferrosilicon according to claim 1 which is useful as a constituent added to steel for the manufacture of magnetic sheet metals.

* * * * *